United States Patent
Refior et al.

(10) Patent No.: US 6,948,503 B2
(45) Date of Patent: Sep. 27, 2005

(54) ELECTROSURGICAL GENERATOR AND METHOD FOR CROSS-CHECKING OUTPUT POWER

(75) Inventors: Tim Refior, Parker, CO (US); Jim Pantera, Brighton, CO (US)

(73) Assignee: ConMed Corporation, Utica, NY (US)

( * ) Notice: Subject to any disclaimer, the term of this patent is extended or adjusted under 35 U.S.C. 154(b) by 133 days.

(21) Appl. No.: 10/299,988

(22) Filed: Nov. 19, 2002

(65) Prior Publication Data

US 2004/0097915 A1 May 20, 2004

(51) Int. Cl.⁷ .............................................. A61B 18/04
(52) U.S. Cl. .................................... 128/898; 606/34
(58) Field of Search ........................ 606/32–35, 37–41

(56) References Cited

U.S. PATENT DOCUMENTS

| | | | |
|---|---|---|---|
| 4,281,373 A | * | 7/1981 | Mabille ........................ 363/97 |
| 4,416,276 A | | 11/1983 | Newton et al. |
| 4,416,277 A | | 11/1983 | Newton et al. |
| 4,574,801 A | | 3/1986 | Manes |
| 4,651,280 A | | 3/1987 | Chang et al. |
| 4,658,819 A | | 4/1987 | Harris et al. |
| 4,712,544 A | | 12/1987 | Ensslin |
| 4,727,874 A | * | 3/1988 | Bowers et al. ................ 606/38 |
| 4,819,752 A | | 4/1989 | Zelin |
| 4,848,335 A | | 7/1989 | Manes |
| 5,087,257 A | | 2/1992 | Farin et al. |
| 5,300,068 A | | 4/1994 | Rosar et al. |
| 5,318,563 A | | 6/1994 | Malis et al. |
| 5,370,645 A | | 12/1994 | Klicek et al. |
| 5,372,596 A | | 12/1994 | Klicek et al. |
| 5,422,567 A | | 6/1995 | Matsunaga |
| 5,423,810 A | | 6/1995 | Goble et al. |
| 5,520,633 A | | 5/1996 | Costin |
| 5,540,681 A | | 7/1996 | Strul et al. |
| 5,573,533 A | | 11/1996 | Strul |
| 5,584,830 A | | 12/1996 | Ladd et al. |
| 5,599,344 A | | 2/1997 | Paterson |
| 5,733,281 A | | 3/1998 | Nardella |
| 5,830,212 A | | 11/1998 | Cartmell et al. |
| 6,139,546 A | | 10/2000 | Koenig et al. |
| 6,165,173 A | | 12/2000 | Kamdar et al. |
| 6,210,403 B1 | | 4/2001 | Klicek |
| 6,228,079 B1 | | 5/2001 | Koenig |
| 6,231,569 B1 | | 5/2001 | Bek et al. |
| 6,261,286 B1 | | 7/2001 | Goble et al. |
| 6,293,941 B1 | | 9/2001 | Strul et al. |
| 6,309,386 B1 | | 10/2001 | Bek |
| 6,398,779 B1 | | 6/2002 | Buysse et al. |

FOREIGN PATENT DOCUMENTS

GB     2154881     9/1985

OTHER PUBLICATIONS

International Search Report for the PCT application PCT/US 03/33784 which corresponds to the present U.S. application.
H. Hölscher et al., *Microcomputers in Safety Technique, An Aid to Orientation for Developer and Manufacturer*, 1986, Chapter 1–1 through 8–9.

* cited by examiner

*Primary Examiner*—Rosiland Rollins
(74) *Attorney, Agent, or Firm*—John R. Ley

(57) ABSTRACT

The functionality and the output power delivered are evaluated in an electrosurgical generator by calculating first and second values related to the output power delivered by using separate first and second computations. The two calculated values are compared, and an error condition is indicated when the two values differ by a predetermined amount. The separate computations, coupled with the other separate activities of measuring, averaging and sampling the output current and voltage measurements, serve as an effective basis for detecting errors caused by malfunctions or equipment failure. The error condition may be used to as a basis to terminate the output power delivery or indicate the error.

40 Claims, 5 Drawing Sheets

ELECTROSURGICAL GENERATOR AND METHOD FOR CROSS-CHECKING OUTPUT POWER

CROSS REFERENCE TO RELATED INVENTION

This invention and application is related to an invention for an Electrosurgical Generator and Method with Multiple Semi-Autonomously Executable Functions, described in U.S. patent application Ser. No. 10/299,953, and for an Electrosurgical Generator and Method for Cross Checking Mode Functionality, described in U.S. patent application Ser. No. 10/299,952, both of which are filed concurrently herewith and assigned to the assignee of the present invention. The subject matter of these concurrently filed application is incorporated herein by this reference.

FIELD OF THE INVENTION

This invention generally relates to electrosurgery. More specifically, the invention relates to a new and improved electrosurgical generator and method that cross-checks the amount of the electrosurgical power delivered to assure proper functionality of the electrosurgical generator and that the desired amount of electrosurgical power is delivered during the surgical procedure.

BACKGROUND OF THE INVENTION

Electrosurgery involves applying relatively high voltage, radio frequency (RF) electrical power to tissue of a patient undergoing surgery, for the purpose of cutting the tissue, coagulating or stopping blood or fluid flow from the tissue, or cutting or coagulating the tissue simultaneously. The high voltage, RF electrical power is created by an electrosurgical generator, and the electrical power from the generator is applied to the tissue from an active electrode manipulated by a surgeon during the surgical procedure.

The amount and characteristics of the electrosurgical energy delivered to the patient is determined by the surgeon and depends on the type of procedure, among other things. For example, cutting is achieved by delivering a continuous RF signal ranging up to relatively high power, for example 300 watts. Coagulation is achieved by rapidly switching the RF power on and off in a duty cycle. The coagulation duty cycle has a frequency considerably lower than the RF power delivered. However, during the on-time of each duty cycle, the electrical power is delivered at the RF frequency. The power delivered during coagulation is typically in the neighborhood of approximately 40–80 watts, although power delivery as low as 10 watts or as high as 110 watts may be required. Simultaneous cutting and coagulation, which is also known as a "blend" mode of operation, also involves a duty cycle delivery of RF energy, but the on-time of the duty cycle during blend is greater than the on-time of the duty cycle during coagulation. Power is delivered at the RF frequency because the frequency is high enough to avoid nerve stimulation, thereby allowing the tissue to remain somewhat stationary without contractions caused by the electrical energy.

The electrosurgical generator must also have the capability to deliver a relatively wide range of power. The resistance or impedance of the tissue may change radically from point-to-point during the procedure, thereby increasing the power regulation requirements for the electrosurgical generator. For example, a highly fluid-perfused tissue, such as the liver, may exhibit a resistance or impedance in the neighborhood of 40 ohms. Other tissue, such as the marrow of bone, may have an impedance in the neighborhood of 900 ohms. The fat or adipose content of the tissue will increase its impedance. The variable characteristics of the tissue require the electrosurgical generator to be able to deliver effective amounts of power into all types of these tissues, on virtually an instantaneously changing basis as the surgeon moves through and works with the different types of tissues at the surgical site.

These wide variations in power delivery encountered during electrosurgery impose severe performance constraints on the electrosurgical generator. Almost no other electrical amplifier is subject to such rapid response to such widely varying power delivery requirements. Failing to adequately regulate and control the output power may create unnecessary damage to the tissue or injury to the patient or surgical personnel. In a similar manner, failing to adequately establish the electrical characteristics for cutting, coagulating or performing both procedures simultaneously can also result in unnecessary tissue damage or injury.

Almost all electrosurgical generators involve some form of output power monitoring circuitry, used for the purpose of controlling the output power. The extent of power monitoring for regulation purposes varies depending upon the type of mode selected. For example, the coagulation mode of operation does not generally involve sensing the voltage and current delivered and using those measurements to calculate power for the purpose of regulating the output power. However, in the cut mode of operation, it is typical to sense the output current and power and use those values as feedback to regulate the power delivered.

In addition to power regulation capabilities, most electrosurgical generators have the capability of determining error conditions. The output power of the electrosurgical generator is monitored to ensure that electrosurgical energy of the proper power content and characteristics is delivered. An alarm is generated if an error is detected. The alarm may alert the surgeon to a problem and/or shut down or terminate power delivery from the electrosurgical generator.

Certain types of medical equipment controlled by microprocessors or microcontrollers utilize multiple processors for backup and monitoring purposes. Generally speaking, one of the processor serves as a control processor to primarily control the normal functionality of the equipment. Another one of the processors serves as a monitor processor which functions primarily to check the proper operation of the control processor and the other components of the medical equipment. Using one processor for primary control functionality and another processor for primary monitoring functionality has the advantage of achieving redundancy for monitoring purposes, because each processor has the independent capability to shut down or limit the functionality of the medical equipment under error conditions. Standards and recommendations even exist for multiple-processor medical equipment which delineates the responsibilities of the safety and monitoring processors.

SUMMARY OF THE INVENTION

The present invention has evolved from a desire to achieve a high degree of reliability for monitoring purposes in a multiple-processor electrosurgical generator. The present invention has also evolved from realizing that control and monitoring functionality, as well as the components used for monitoring conditions, need to be cross-checked on a continual and relatively frequently recurring basis to ensure proper functionality in the context of the rapidly and widely varying output requirements of an electrosurgical generator. In addition, the present invention advantageously monitors output power in an electrosurgical generator by using multiple processors not only for the purpose of controlling the electrosurgical generator from an output power regulation standpoint, but also for the purpose of checking proper functionality of the processors and their other associated equipment on a general basis.

In accordance with these improvements, the present invention involves a method of evaluating the functionality of an electrosurgical generator and the electrosurgical output power delivered by the generator. A first value related to the output power delivered is calculated using a first computation, and a second value related to the output power delivered is calculated using a second computation. The first and second values are compared, and an error condition is indicated when the first and second values differ by a predetermined amount. Preferably, separate measurements of the voltage and current of the power delivered are used in performing the first and second computations, the first and second values are average values calculated over different predetermined periods of time, and the two output current and the output voltage measurements are sampled at different sampling frequencies for calculating the first value with the first computation. The separate computations of the first and second values, coupled with the other preferable separate activities of measuring, averaging and sampling the output current and voltage measurements, contribute an effective basis for cross-checking the proper functionality and power output of the electrosurgical generator, and taking action to prevent risks to the patient from improper power delivery or other improper functionality of the generator under such error conditions.

Another method of evaluating the functionality and output power delivered, which also obtains the same benefits and improvements, involves activating the electrosurgical generator to deliver the output power, sensing the current and the voltage at first periodic intervals to obtain a first set of measurements of the current and voltage of the output power delivered, sensing the current and the voltage at second periodic intervals to obtain a second set of measurements of the current and voltage of the output power delivered, recording the first and second sets of measurements, deactivating the electrosurgical generator to terminate the delivery of the output power, calculating a first value related to the output power delivered from the first sets of recorded measurements by executing a first computation with the control processor, calculating a second value related to the output power delivered from the second sets of recorded measurements by executing a second computation with the monitor processor, comparing the calculated first and second values to determine whether the calculated first and second values differ by a predetermined amount, and executing an error response upon determining that the calculated first and second values differ by the predetermined amount.

The present invention also involves an improved electrosurgical generator having the capability of evaluating its own functionality and the output power delivered. A plurality of sensors sense current and voltage of the output power delivered and supply current and voltage measurement signals related to the amount of current and voltage sensed. A control processor receives the current and voltage measurement signals and performs a first computation based on the current and voltage measurement signals to derive power regulation feedback information and to derive a first value related to the output power delivered. A monitor processor receives the current and voltage measurement signals and performs a second computation separate from the first computation to derive a second value related to the output power delivered. A communication path connects the control and monitor processors by which to communicate information including the first and second values between the processors. One of the control or monitor processors functions as a comparison processor to execute a comparison procedure for comparing the first and second values and delivering an error condition signal when the first and second values differ by a predetermined amount. The electrosurgical generator responds to an assertion of the error condition signal by either issuing an error indication and/or terminating the delivery of output power. Preferable features of the electrosurgical generator include individual sensors for deriving independent current measurement and independent voltage measurement signals used in the two computations. Another preferable feature of the electrosurgical generator is a direct memory access (DMA) technique of reading digital forms of the current and voltage measurement signals into memory, and thereafter reading those signals from memory to perform the two computations. The separate computations, coupled with the other preferable individual measurements of the output current and voltage, permit the electrosurgical generator to cross-check its own functionality and power output, and to take appropriate action to prevent risks to the patient if a discrepancy is detected.

A more complete appreciation of the present disclosure and its scope, and the manner in which it achieves the above noted improvements, can be obtained by reference to the following detailed description of presently preferred embodiments taken in connection with the accompanying drawings, which are briefly summarized below, and the appended claims.

DETAILED DESCRIPTION

Figure 1:
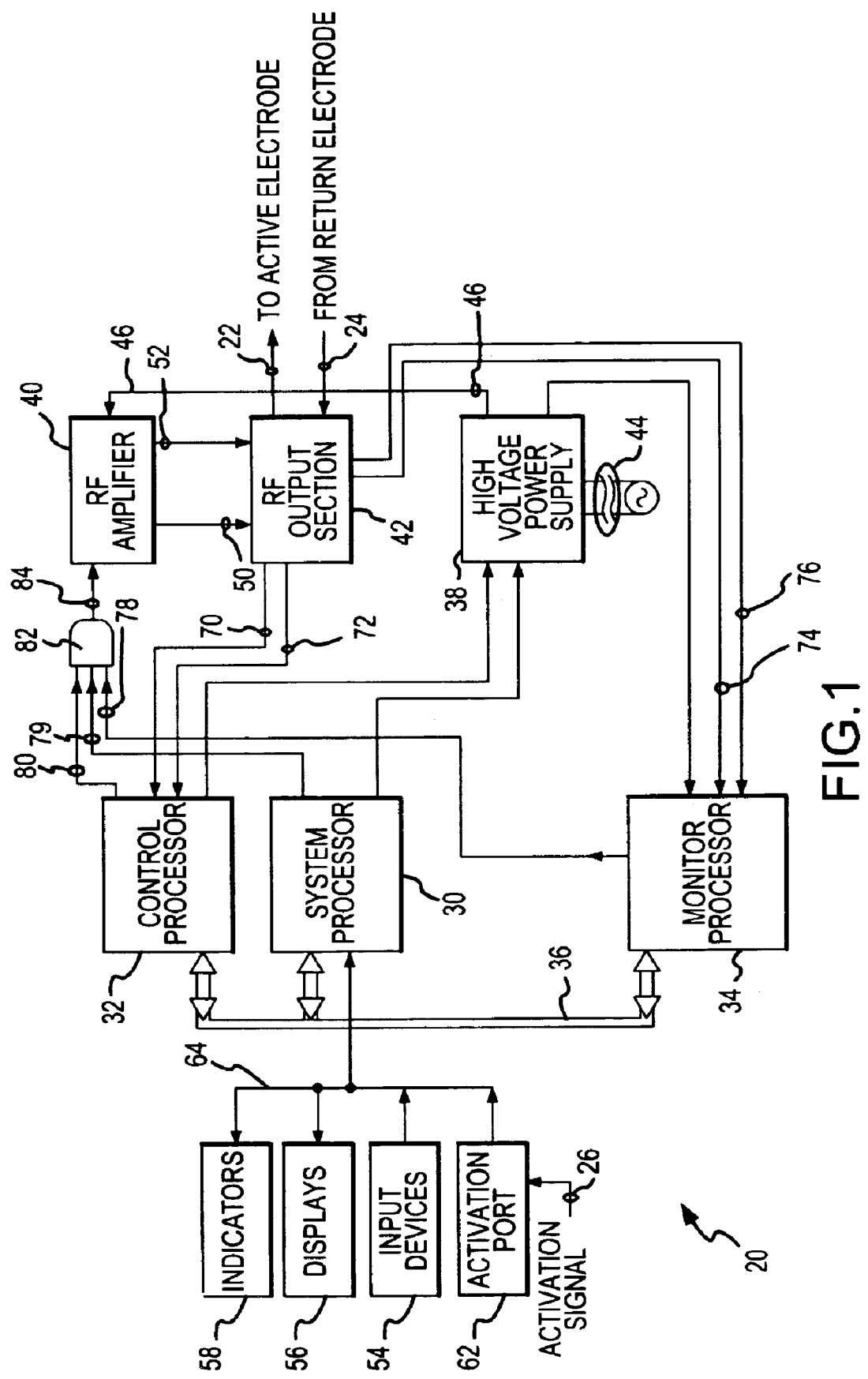
FIG. 1 is a block diagram of a multiple processor electrosurgical generator incorporating the present invention.

An electrosurgical generator 20, shown in FIG. 1, supplies electrosurgical output voltage and output current at 22, which is conducted to an active electrode (not shown) for monopolar and bipolar electrosurgery. Current is returned at 24 to the electrosurgical generator 20 from a return electrode (not shown), after having been conducted through the tissue of the patient. The generator is activated to deliver the electrosurgical output power at 22 by an activation signal supplied at 26. The activation signal 26 is asserted upon closing a switch on a handpiece (not shown) which supports the active electrode and is held by the surgeon. The activation signal 26 may also be asserted from a conventional foot switch (not shown) which is depressed by foot pressure from the surgeon.

The electrosurgical generator 20 includes a system processor 30, a control processor 32, and a monitor processor 34. The system processor 30 generally controls the overall functionality of the electrosurgical generator 20. The system processor 30 includes nonvolatile memory (not shown) containing programmed instructions to be downloaded to the other processors 32 and 34 to establish the functionality of the control and monitor processors 32 and 34, as well as the entire functionality of the electrosurgical generator 20. The processors 30, 32 and 34 communicate with each other over a system bus 36. In general, the system processor 30 supervises and controls, at a high level, the entire electrosurgical generator 20.

The primary functionality of the control processor 32 is to establish and regulate the power delivered from the electrosurgical generator at 22. The control processor 32 is connected to a high voltage power supply 38, an RF amplifier 40, and an RF output section 42. The high voltage power supply 38 generates a DC operating voltage by rectifying conventional alternating current (AC) power supplied by conventional mains power lines 44, and delivers the DC operating voltage to the RF amplifier 40 at 46. The RF amplifier 40 converts the DC operating voltage into monopolar drive signals 50 and bipolar drive signals 52 having an energy content and duty cycle appropriate for the amount of power and the mode of electrosurgical operation which have been selected by the surgeon. The RF output section 42 converts the monopolar and bipolar drive signals 50 and 52 into the RF voltage and current waveforms and supplies those waveforms to the active electrode at 22 as the output power from the electrosurgical generator.

The basic function of the monitor processor 34 is to monitor the functionality of the high voltage power supply 38 and the RF output section 42, as well as to monitor the functions of the system processor 30 and the control processor 32. If the monitor processor 34 detects a discrepancy in the output electrosurgical energy, or a discrepancy in the expected functionality of the system processor 30 or the control processor 32, a failure mode is indicated and the monitor processor 34 terminates the delivery of output electrosurgical energy from the electrosurgical generator 20.

The processors 30, 32 and 34 are conventional microprocessors, microcontrollers or digital signal processors, all of which are essentially general purpose computers that have been programmed to perform the specific functions of the electrosurgical generator 20.

The electrosurgical generator 20 also includes user input devices 54 which allow the user to select the mode of electrosurgical operation (cut, coagulation or a blend of both) and the desired amount of output power. In general, the input devices 54 are dials and switches that the user manipulates to supply control, mode and other information to the electrosurgical generator. The electrosurgical generator 20 also includes information output displays 56 and indicators 58. The displays 56 and indicators 58 provide feedback, menu options and performance information to the user. The input devices 54 and the output displays 56 and indicators 58 allow the user to set upland manage the operation of the electrosurgical generator 20.

The activation signals at 26 are applied from the finger and foot switches to an activation port 62. The system processor 30 reads the activation signals 26 from the port 62 to control the power delivery from the electrosurgical generator 20. The components 54, 56, 58 and 62 are connected to and communicate with the system processor 30 by a conventional input/output (I/O) peripheral bus 64, which is separate from the system bus 36.

In order to continually monitor the power delivered, as well as to achieve a high degree of reliability and redundancy for safety monitoring purposes, the control processor 32 and the monitor processor 34 each independently calculate the power delivered from the RF output section 42. The independent power calculations are thereafter compared, by at least one of the three processors 30, 32 and 34, and if a discrepancy is noted, the comparing processor signals the system processor 30 of the discrepancy, and the power delivery from the electrosurgical generator 20 is shut down and/or an error is indicated.

The power calculations performed by the control processor 32 are part of the normal functionality of the control processor in regulating the output power. The control processor 32 receives an output current signal 70 and an output voltage 72 from the RF output section 42. The control processor calculates the amount of output power by multiplying the current and voltage signals 70 and 72 to obtain the power output. The monitor processor 34 receives an output current signal 74 and an output voltage signal 76. The output current and voltage signals 74 and 76 are derived independently of the output current and voltage signals 70 and 72, by separate current and voltage sensors. The monitor processor 34 calculates the output power based on the output current and voltage signals 74 and 76. The power-related calculations performed by the control processor 32 and by the monitor processor 34 are not necessarily performed at the same frequency or at exactly the same time, although the power calculations must be sufficiently related in time so as to be comparable to one another.

The separately-calculated power related information is periodically compared by one or more of the processors 30, 32 or 34, preferably in either the system processor 30 or the monitor processor 34. To make the comparison, the calculated power information is communicated over the system bus 36 to the processor which performs the comparison. If the comparison shows similar power calculations within acceptable limits, proper functionality of the electrosurgical generator 20 is indicated. If the comparison shows dissimilar power calculations outside of acceptable limits, safety related issues are indicated. Dissimilar power calculations may indicate that one of the control or monitor processors 32 or 34 is malfunctioning, or some of the components used in connection with the processors are malfunctioning, or a failure in one of the current and voltage sensors which supply the current and voltage signals 70, 72, 74 and 76, among other things. In general, the response to an issue indicated by a power calculation discrepancy will result in indication of an error condition and/or the termination of power delivery from the electrosurgical generator 20. Information will also be supplied to and presented at the displays 56 and indicators 58 describing the error condition.

Each of the processors 30, 32 and 34 has the capability to exercise control over the delivery of power from the electrosurgical generator. The monitor processor 34 and the system processor 30 assert enable signals 78 and 79 to an AND logic gate 82. The control processor 30 asserts a drive-defining signal 80 to the logic gate 82. The drive-defining signal 80 is passed through the logic gate 82 and becomes a drive signal 84 for the RF amplifier 40, so long as the enable signals 79 and 80 are simultaneously presented to the logic gate 82. If either the system processor 30 or the monitor processor 34 de-asserts its enable signal 79 or 78, respectively, the logic gate 82 will terminate the delivery of the drive signal 84, and the RF amplifier 80 will cease to deliver monopolar and bipolar drive signals 50 and 52, resulting in terminating the delivery of electrosurgical power from the generator 20 at 22. Because the control processor 32 develops the drive-defining signal 80 to control the output power of the electrosurgical generator, the control processor 82 can simply de-assert the drive-defining signal 80 to cause the electrosurgical generator to cease delivering output power. Thus, any of the processors 30, 32 or 34 as the capability to shut down or terminate the delivery of power from the electrosurgical generator under conditions of significant discrepancies in the independently-calculated power output by de-asserting the signals 79, 80 or 82, respectively.

Figure 2:
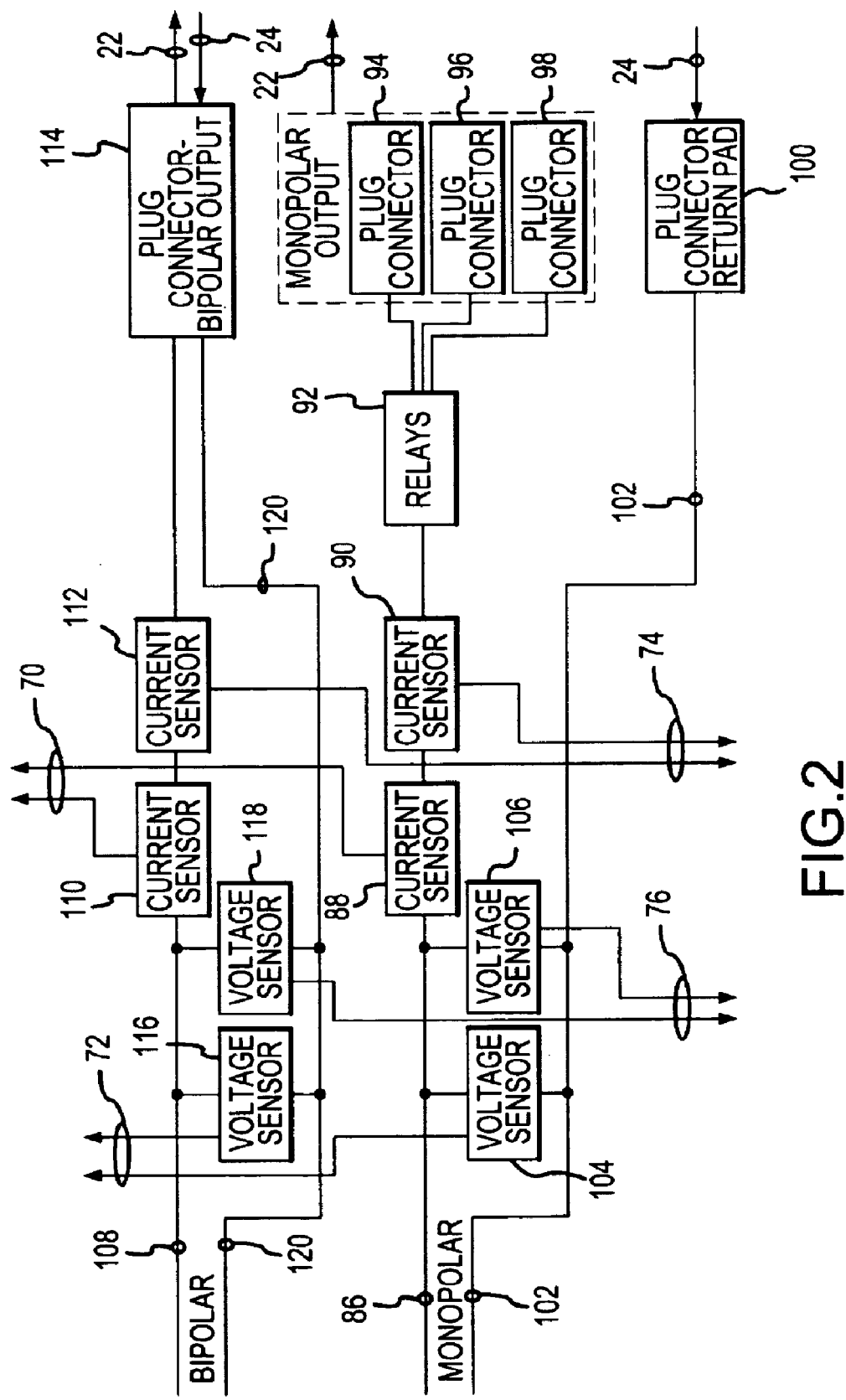
FIG. 2 is a block diagram of a portion of an RF output section of the electrosurgical generator shown in FIG. 1.

More details concerning the derivation of the output current and output voltage sense signals 70, 72, 74 and 76 are understood by reference to FIG. 2, which illustrates a portion of the RF output section 42 (FIG. 1). The flow path for the monopolar electrosurgical current is through a delivery conductor 86, through series-connected current sensors 88 and 90, through relays 92 and to one or more plug connectors 94, 96 or 98 which are selected by the relays 92. The monopolar electrosurgical current flows from the plug connectors 94, 96 and 98 to the active electrode at 22. The return path for the monopolar electrosurgical current is from the electrical return electrode (not shown) at 24 to a return plug connector 100 to which the return electrode (sometimes referred to as a return pad) is connected. The return current flows through a return conductor 102. Voltage sensors 104 and 106 are connected between the delivery conductor 86 and the return conductor 102 to sense the voltage at which the monopolar electrosurgical output power is delivered.

The current sensor 88 delivers the output current sense signal 70 to the control processor 32 (FIG. 1), and the current sensor 90 delivers the output current sense signal 74 to the monitor processor 34 (FIG. 1). In a similar manner, the voltage sensor 104 delivers the output voltage sense signal 72 to the control processor 32 (FIG. 1), and the voltage sensor 106 delivers the output voltage sense signal 76 to the monitor processor 34 (FIG. 1). Arranged in this manner, the current sensors 88 and 90, and the voltage sensors 104 and 106 supply their own sense signals, independently of sense signals supplied by the other sensors. Any adverse functionality of one of the sensors will not therefore affect the functionality of the other sensors.

The flow path of the bipolar electrosurgical current is from a first bipolar delivery conductor 108, through series-connected current sensors 110 and 112 and to a bipolar output plug connector 114. The bipolar electrosurgical current flows from the plug connector 114 to the active electrode at 22 and returns from the return electrode at 24. The return current flows from the bipolar output plug connector 114 through a second bipolar conductor 120. Voltage sensors 116 and 118 are connected between the first and second bipolar delivery conductors 108 and 120 and therefore sense the voltage at which the bipolar electrosurgical output power is delivered.

The current sensor 110 delivers the output current sense signal 70 to the control processor 32 (FIG. 1), and the current sensor 112 delivers the output current sense signal 74 to the monitor processor 34 (FIG. 1). In a similar manner, the voltage sensor 116 delivers the output voltage sense signal 72 to the control processor 32 (FIG. 1), and the voltage sensor 118 delivers the output voltage sense signal 76 to the monitor processor 34 (FIG. 1). Arranged in this manner, the current sensors 110 and 112, and the voltage sensors 116 and 118 supply their own sense signals, independently of sense signals supplied by the other sensors. Again, adverse functionality of one of the sensors will not therefore affect the functionality of the other sensors.

Only one set of the current sense signals 70 and 74 and only one set of the voltage sense signals 72 and 76 will be supplied when the electrosurgical generator is operating in either the monopolar or the bipolar mode. In other words, it is not possible for the electrosurgical generator to operate in both the monopolar and the bipolar mode simultaneously under normal operating conditions. Each of the sensors 116, 118, 104, 106, 110, 112, 88 and 90 is preferably a conventional transformer.

Figure 3:
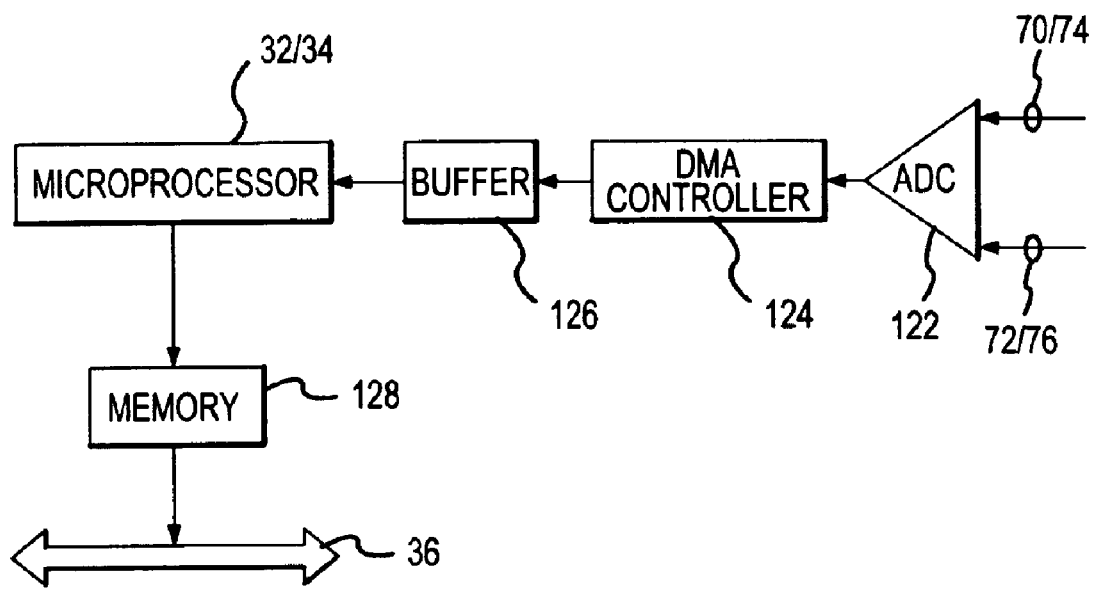
FIG. 3 is a block diagram illustrating signal and information flow during a output power monitoring by one of the processors of the electrosurgical generator shown in FIG. 1.

The current sense signals 70 and 74, and the voltage sense signals 72 and 76 are applied to and dealt with by the control processor 32 and the monitor processor 34, respectively, each in the similar manner shown in FIG. 3. The current and voltage sense signals 70 (74) and 72 (76) are supplied from the RF output section 42 (FIGS. 2 and 1) to a conventional analog to digital converter (ADC) 122. The ADC 122 converts the instantaneous values of the analog current and voltage sense signals 70 (74) and 72 (76) into sample values at sampling intervals established by control signals supplied by the microprocessor 32 (34). The sample values of the current and voltage sense signals 70 (74) and 72 (76) are stored in a conventional buffer memory 126 at sequential addresses established by a conventional direct memory access (DMA) controller 124. The ADC 122 and the DMA controller 124 operate on semi-autonomous basis to store the sample values of the current and voltage sense signals in the buffer 126. One exemplary sampling technique that may be effectively employed in the present invention is described in greater detail in the first above-identified U.S. patent application filed concurrently herewith.

After a predetermined number of sample values of the current and voltage sense signals 70 (74) and 72 (76) have been stored in the buffer 126, the microprocessor 32 (34) reads those values and thereafter calculates power-related information. After reading the values of the current and voltage sense signals from the buffer 126, the DMA controller 124 replaces those values in the buffer 126 with new values supplied by the ADC 122.

The power-related information is preferably root mean square (RMS) output power or some value related to RMS output power. One preferred technique for calculating the power-related information is for the microprocessor 32 (34) to square each of the instantaneous sample values of the current and voltage sense signals 70 (74) and 72 (76), sum all of the squared current sample values, sum all of the squared voltage sample values, multiply together the sum of the squared voltage sample values and the sum of the squared current sample values, and take the square root of the product obtained from the multiplication. This example of a calculation is not true RMS power, because no step was performed to divide by the number of collected samples. However, the resulting power-related information is directly related to RMS power because the number of samples taken and used in the calculation is the same. Other types of mathematical calculations may be performed to obtain the power-related information in accordance with the present invention. One exemplary to calculation technique for determining power-related information is described in greater detail in the first above-identified U.S. patent application filed concurrently herewith. Other power-related information calculation algorithms can also be employed with the present invention.

Calculating power by obtaining a plurality of sample values over a predetermined time effectively integrates the power-related information. This is particularly advantageous in view of the typical manner in which an electrosurgical generator is activated by the surgeon. The typical activation procedure is for the surgeon to depress the finger control switch or step on the foot switch only for a few seconds at a time to perform a series of relatively short and continually repetitive surgical actions during the entire electrosurgical procedure. Collecting samples over a relatively long period of time permits integration and long-time digital filtering of the values resulting from each of these short activations as a type of filtering to eliminate anomalous effects.

With similar voltage and current sense signals, the control processor 32 and the monitor processor 34 should each calculate almost the same amount of power. Some small difference between the calculated values may occur due to timing considerations for each of the signals or slight differences in the sensors or in the signal paths for each of the signals. Thus, the comparison looks for the two results to be almost the same within an acceptable tolerance that may be determined empirically.

After performing the calculations, the results are stored in a memory 128 or held in the processor performing the calculation. The memory 128 is connected to the system bus 36 so that the results of the calculations stored in the memory 128 can be read by one or more of the other processors which are also connected to the system bus 36.

To perform the comparison of the calculated power-related results, the calculated power-related results are communicated over the system bus 36 to the system processor 30 or to either the control processor 32 or the monitor processor 34 (FIG. 1). Either the system processor 30 or the monitor processor 34 (FIG. 1) should perform the comparison, to obtain a redundancy check on the operation of the control processor 32 (FIG. 1) which must make the calculation to regulate the output power. However, depending upon the capability of the control processor 32, it may perform the comparison of the power-related information. The processor which performs the comparison, hereinafter referred to as the "comparison processor," receives the calculated power information from the memory 128 of the control processor 32 and the monitor processor 34 to perform the comparison.

Figure 4:
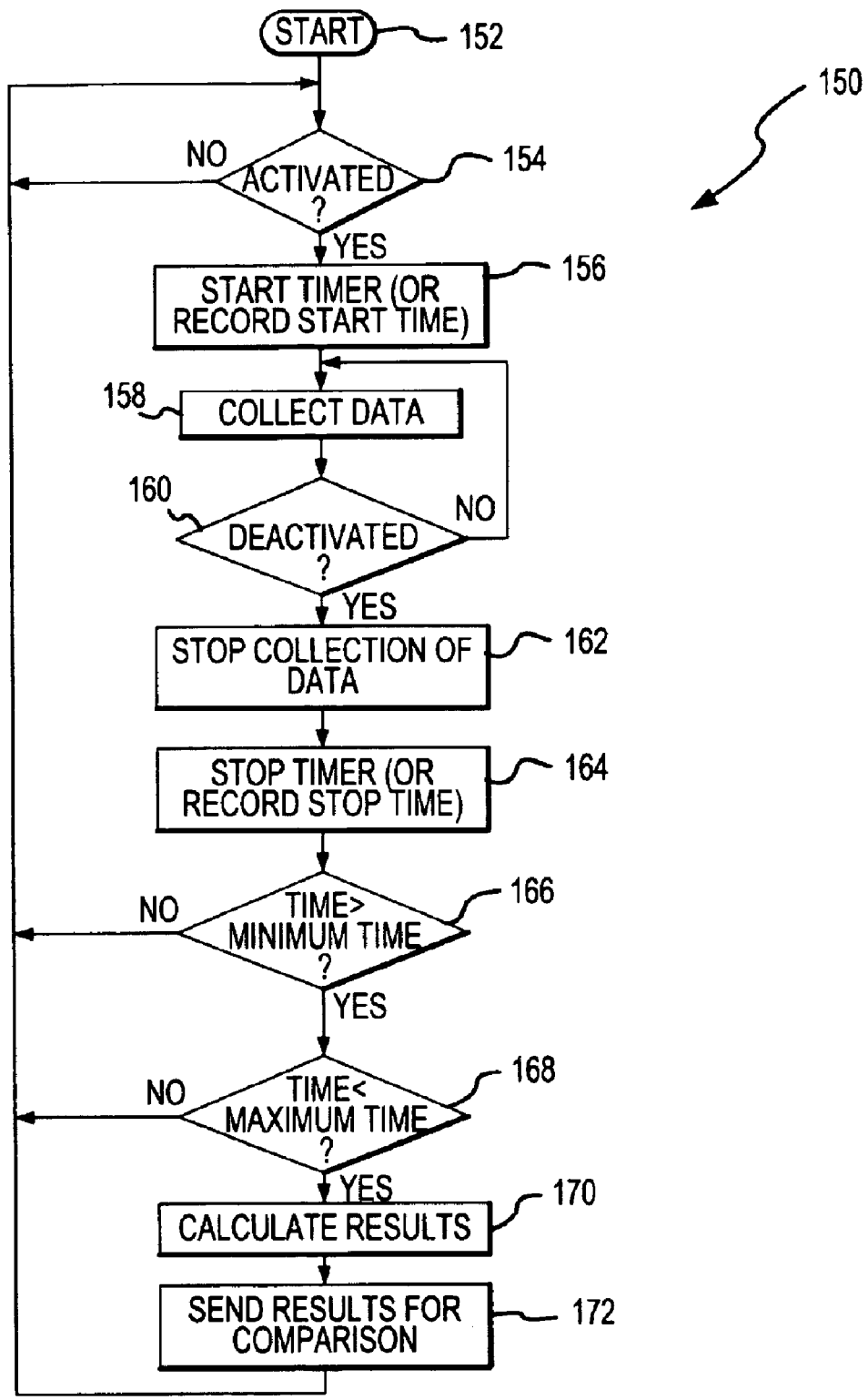
FIG. 4 is a flow chart for a procedure for generating information used for monitoring power output and creating information, executed by the components shown in FIGS. 2 and 3 of the electrosurgical generator shown in FIG. 1.

An exemplary and more detailed explanation of the process flow or procedure 150 used by the control and monitor processors 32 and 34 to calculate the power-related information from the sampled current and voltage values is shown in FIG. 4. The procedure 150 starts at step 152. At step 154 it is determined whether the electrosurgical generator has been activated, by the delivery of the activation signal 26 (FIG. 1). Until activation, the procedure 150 waits at step 154. Once activation occurs, either a timer is started or the current time (a start time) is recorded, and shown at step 156. The processor is able to measure or calculate the duration of the activation. The sample values of the current and voltage signals are collected at step 158 until the electrosurgical generator is determined to be de-activated at step 160. At step 158, the ADC 122 converts the analog values of the current and voltage sense signals to their digital sampled values, and the DMA controller 124 stores the instantaneous sampled values generated by the ADC 122 in the buffer memory 126 (FIG. 3). This occurs until the electrosurgical generator is de-activated at step 160 or until the buffer memory 126 is filled with samples. Upon deactivation at step 160, the collection of the sampled values (data) is stopped at step 162. Thereafter at step 164, the timer is stopped or the current time (a stop time) is recorded.

If the time duration during which the electrosurgical generator was activated is not within a predetermined window of time, as determined at steps 166 and 168, then the power-related information calculations are not performed. Instead, the procedure 150 returns to step 154 to wait for the next activation. In this manner, certain common events which typically do not involve the delivery of the electrosurgical power during an actual procedure will not result in an inadvertent, unnecessary shutdown of the electrosurgical generator. For example, some surgeons momentarily short-circuit the output power terminals of the electrosurgical generator to observe an arc as a technique for determining whether the electrosurgical generator is operating. While this is not recommended procedure, it does indicate to the surgeon that the electrosurgical generator is working. Since there is no tissue resistance or impedance, the current and voltage sense signals current and voltage sense signals 70 (74) and 72 (76) are anomalous. Such anomalies could cause such a large discrepancy in the calculated power-related information such that, when the comparison is made, an error is detected, when in fact, there was no actual error. Also, either the control processor 32 or the monitor processor 34 may miss part or all of a power delivery event that is too short. In a similar manner, the maximum time duration of the predetermined window of time determined at step 168 is used to obtain accurate samples during the activation time by preventing inordinately long activations of the electrosurgical generator from delivering so many sampled values of the sensed voltage and current to the buffer 126 (FIG. 3) to cause it to overflow.

Thus, the predetermined window of time, established at steps 166 and 168, enables the procedure 150 to prevent an inadvertent shutdown of the electrosurgical generator 20 in anomalous situations. The size of the window is selected based on an empirical data concerning of the typical duration of most electrosurgical procedures, which usually fall within a range of minimum and maximum times (e.g. 0.5–5.0 seconds, respectively). The size of the buffer 126 and the sampling rate of the ADC 122 (FIG. 3) may also define the maximum time limit at step 168 over which data may be collected, although the results of filling numerous buffers may also be accumulated if information is collected over a longer time period. The predetermined window of time is fixed by a minimum time, established at step 166, and a maximum time, established at step 168, and these minimum and maximum times define the preferred time frame for which the power-related information is obtained.

If the duration of the electrosurgical procedure is within the predetermined window of time, as determined at steps 166 and 168, then the various calculations for RMS voltage, current and power are performed at step 170. The power-related results of the calculations are then sent, at step 172, to the comparison processor to perform the comparison of the results. The procedure 150 then returns to step 154.

As an alternative to determining whether the activation of the electrosurgical generator is within the predetermined window of time at steps 166 and 168, the RMS calculations may be done by the control and monitor processors regardless of the duration of the activation. In this case, the comparison processor makes a determination of whether to eliminate the comparison if the duration is outside the window.

Figure 5:
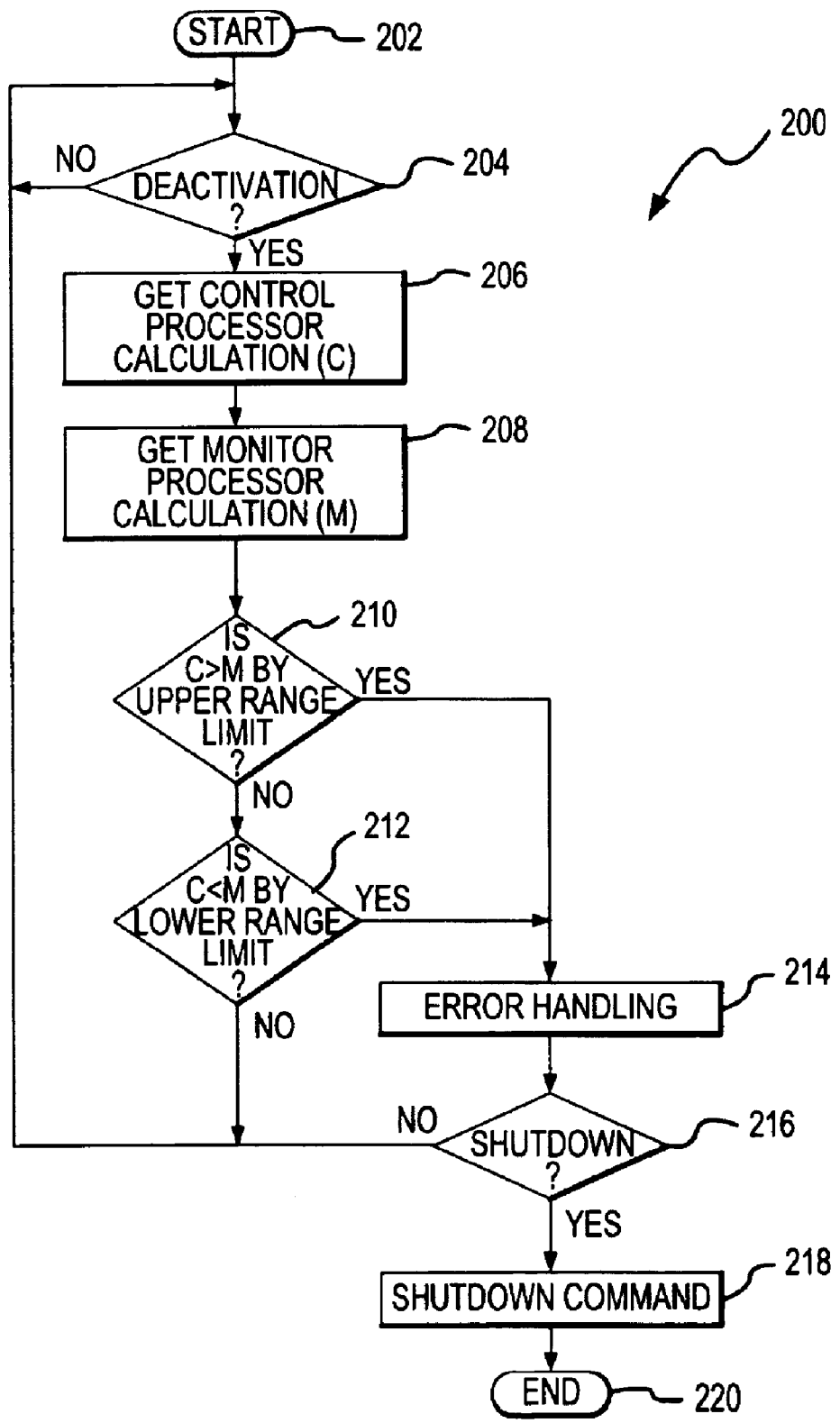
FIG. 5 is a flow chart for a procedure for communicating, analyzing and responding to the information generated by the procedure shown in FIG. 4.

An exemplary and more detailed explanation of a process flow or procedure 200 for making the comparison between the calculated power-related information from the control and monitor processors, and responding, is shown in FIG. 5. The procedure 200 starts at step 202. At step 204 a determination is made whether the electrosurgical generator has been de-activated. So long as deactivation exists, the procedure 200 waits at step 204. Once activation occurs, the determination at 204 is affirmative, and the calculated power-related information is read from the memories 128 (FIG. 3) of the control processor 32, at step 206, and from the memories 128 of the monitor processor 34, at step 208, or otherwise supplied by the two calculating processors. If either the control processor or the monitor processor is the comparison processor, it may or may not actually store the results of the power calculations in its associated memory 128, while performing the procedure 200.

At steps 210 and 212 respectively, it is determined whether the two calculated results are within an acceptable tolerance of each other. If the calculated result (C) from the control processor 32 is not greater than the calculated result (M) from the monitor processor 34 by a predetermined upper range limit, as determined at step 210, and if the calculated result (C) is not less than the calculated result (M) by a predetermined lower range limit, as determined at step 212, then the procedure 200 returns to step 204 to wait for the end of the next activation. Negative determination at steps 210 and 212 indicate acceptable functionality. On the other hand, if the two calculated results (C) and (M) are not within an acceptable tolerance of each other, as determined at steps 210 and 212, then an appropriate error handling procedure is performed at step 214.

The error handling procedure may log or count each occurrence of the error, alert the surgeon, shut down the electrosurgical generator and/or take any other appropriate responsive measures. Counting the occurrence of errors may enable other responsive measures after a certain number or threshold of errors occurs sequentially or some number of errors occurs within a larger number of activations or attempts to activate, for example, 5 errors out of 10 attempted activations. If the error response does not include shutting down the electrosurgical generator, as determined at step 216, then the procedure 200 returns to step 204 to wait for the end of presently occurring activation. If, on the other hand, the response does include shutting down the electrosurgical generator, as determined at step 216, then a command to shut down the electrosurgical generator is issued at step 218, and the procedure 200 ends at step 220.

The present invention offers the improvement and advantage of determining when a sensor fails. In such circumstances, the current or voltage sense signal from the failed sensor will result in a power-related calculation which does not compare favorably with the other power-related calculation, thereby indicating a safety-related issue with the electrosurgical generator. Additionally, the present invention can detect whether there is a failure in certain other components associated with the control and monitor microprocessors. Such a failure would also result in a discrepancy between the calculated results because the failed component will generally not properly pass or handle the value of the voltage and current signals which flow through that failed component. Moreover, should either of the controller or monitor processors fail to execute their programed functionality, such a failure is also likely to be reflected in erroneous calculations of the power-related information.

The present invention is particularly advantageous in combination when the monitor processor 34 monitors the mode functionality of the electrosurgical generator 20 (FIG. 1). The second aforementioned patent application describes a mode functionality check incorporated in the electrosurgical generator 20. In general terms, the mode functionality check involves observing the characteristics of the drive-defining signal 80 supplied by the control processor 32 to determine whether the control processor 32 is delivering the proper pattern of drive signals indicated by the selected mode of operation. If the characteristics of the drive-defining signal 80 are not consistent with the selected mode of operation, the monitor processor 34 terminates the delivery of electrosurgical power. For example, acceptable power calculations could be obtained even though the electrosurgical generator is operating in an incorrect mode. Since a malfunction could cause an error either in the power delivered or the pattern of drive signals relative to the selected mode of operation, checking both the power delivered and the mode information provides an very effective technique for determining the proper operation of the electrosurgical generator.

Many other benefits, advantages and improvements in monitoring the proper functionality of the electrosurgical generator will also be apparent upon gaining a full appreciation of the present invention. Thus, the electrosurgical generator can be prevented from operating under conditions which might possibly cause a risk to the patient and under conditions where the output power and performance of the electrosurgical generator is more reliably delivered.

Presently preferred embodiments of the invention and its improvements have been described with a degree of particularity. This description has been made by way of preferred example. It should be understood that the scope of the invention is defined by the following claims.

What is claimed is:

1. A method of evaluating functionality of an electrosurgical generator which delivers electrosurgical output power established by an output current and an output voltage, the electrosurgical generator including a control processor which controls the delivery of the electrosurgical output power and also including a monitor processor which monitors one of performance or functions of the electrosurgical generator, comprising:

sensing the output voltage and the output current;

calculating with a first computation a first value related to the output power delivered by using the sensed output current and the sensed output voltage;

calculating with a second computation separate from the first computation a second value related to the output power delivered by using the sensed output current and the sensed output voltage;

comparing the first and second values;

indicating an error condition when the first and second values differ by a predetermined amount;

performing the first calculation using the control processor; and performing the second calculation using the monitor processor.

2. A method as defined in claim 1, further comprising:

sensing the output voltage and the output current separately for use in the first and second computations; and calculating the first value using values of the sensed output voltage and the sensed output current which are separate from values of the sensed output voltage and the sensed output current used in calculating the second value.

3. A method as defined in claim 1, further comprising:

calculating the first and second values as the average power delivered from the electrosurgical generator over a predetermined period of time.

4. A method as defined in claim 3, further comprising:

calculating the first value over a first predetermined period of time;

calculating the second value over a second predetermined period of time; and establishing different first and second predetermined periods of time.

5. A method as defined in claim 3, further comprising:
sensing the output current and the output voltage at a first sampling frequency for calculating the first value with the first computation;
sensing the output current and the output voltage at a second sampling frequency for calculating the second value with the second computation; and
establishing different first and second sampling frequencies.

6. A method as defined in claim 3, further comprising:
activating the electrosurgical generator to deliver the output power during an activation time period; and
using the activation time period as the predetermined period of time over which the average power delivered is calculated as the first and second values.

7. A method as defined in claim 1, further comprising:
communicating the first value to the monitor processor; and
comparing the first and second values using the monitor processor.

8. A method as defined in claim 7, further comprising:
indicating the error condition from the monitor processor.

9. A method as defined in claim 1, wherein the electrosurgical generator further includes a system processor which oversees functionality of the control and monitor processors, and further comprising:
communicating the first and second values to the system processor; and
comparing the first and second values using the system processor.

10. A method as defined in claim 9, further comprising:
indicating the error condition from the system processor.

11. A method as defined in claim 1, further comprising:
sensing the output current by sensing a plurality of current values for each of the first and second computations;
sensing the output voltage by sensing a plurality of voltage values for each of the first and second computations;
performing a root mean square computation on each of the sensed pluralities of current values and on each of the sensed pluralities of voltage values to obtain a root mean square current value of each of the pluralities of sensed current values and to obtain a root mean square voltage value of each of the pluralities of sensed voltage values; and
using the root mean square current values and the root mean square voltage values in the first and second computations to calculate the first and second values.

12. A method as defined in claim 1, further comprising:
terminating delivery of the electrosurgical output power upon indicating an error condition.

13. A method as defined in claim 1, further comprising:
incrementing a count number with each instance where the first and second values differ by more than the predetermined amount; and
indicating the error condition upon the count number reaching a predetermined threshold.

14. A method as defined in claim 13, further comprising:
resetting the count number to a predetermined count value upon the first and second values not differing by the predetermined amount within a predetermined number of most recent comparisons.

15. A method as defined in claim 13, further comprising:
incrementing the count number only with each instance where the first and second values differ by the predetermined amount within a predetermined number of most recent comparisons.

16. A method as defined in claim 1, wherein the electrosurgical generator regulates the amount of output power delivered based on feedback information, and wherein the electrosurgical generator comprises:
a plurality of sensors connected to sense the output current and the output voltage of the output power delivered and operative to supply current and voltage measurement signals related to the amount of output current and output voltage sensed, respectively;
wherein the control processor is receptive of the current and voltage measurement signals and performs the first computation based on the current and voltage measurement signals to derive the feedback information related to the output power delivered and to derive the first value;
wherein the monitor processor is receptive of the current and voltage measurement signals and performs the second computation based on the current and voltage measurement signals to derive the second value;
a communication path connecting the control and monitor processors over which the control and monitor processors communicate information including the first and second values, one of the control or monitor processors receiving the first and second values being a comparison processor;
the comparison processor performing a comparison procedure for comparing the first and second values and delivering an error condition signal when the first and second values differ by the predetermined amount; and
the electrosurgical generator responding to the assertion of the error condition signal by one of either indicating the error condition or terminating the delivery of output power.

17. A method as defined in claim 16, wherein the electrosurgical generator further comprises:
a system processor which oversees functionality of the control and monitor processors, the system processor connected to the communication path to communicate with the control and monitor processors, the system processor rather than the monitor or control processor being the comparison processor which delivers the error condition signal.

18. A method as defined in claim 17, wherein:
the control processor performs the first computation and obtains the first value;
the monitor processor performs the second computation and obtains the second value; and
the control and monitor processors send the first and second values to the system processor over the communication path.

19. A method as defined in claim 16, wherein the plurality of sensors includes:
a first current sensor for supplying a first current measurement signal used by the control processor in performing the first computation;
a second current sensor for supplying a second current measurement signal used by the monitor processor in performing the second computation;
a first voltage sensor for supplying a first voltage measurement signal used by the control processor in performing the first computation; and
a second voltage sensor for supplying a second voltage measurement signal used by the monitor processor in performing the second computation.

20. A method as defined in claim 19, wherein the control and monitor processors are digital processors.

21. A method as defined in claim 20, wherein the electrosurgical generator further comprises:
- a first analog to digital converter (ADC) connected to the first current sensor and to the first voltage sensor and operative to convert the first current measurement signal and the first voltage measurement signal into digital form;
- a first direct memory access (DMA) controller;
- a first buffer connected to the first ADC and to the first DMA controller, the first DMA controller placing the digital forms of the first current measurement signal and the first voltage measurement signal into the first buffer;
- a second analog to digital converter (ADC) connected to the second current sensor and to the second voltage sensor and operative to convert the second current measurement signal and the second voltage measurement signal into digital form;
- a second direct memory access (DMA) controller;
- a second buffer connected to the second ADC and to the second DMA controller, the second DMA controller placing the digital forms of the second current measurement signal and the second voltage measurement signal Into the second buffer; and wherein:
- the control processor is connected to the first buffer to read the digital forms of the first current measurement signal and the first voltage measurement signal from the first buffer to perform the first computation; and
- the monitor processor is connected to the second buffer to read the digital forms of the second current measurement signal and the second voltage measurement signal from the second buffer to perform the second computation.

22. A method as defined in claim 17, wherein the electrosurgical generator further comprises:
- an alarm connected to the system processor and responsive to the error condition signal to deliver an alarm.

23. A method as defined in claim 17, wherein:
- the system processor responds to the error condition signal by logging an error occurrence.

24. A method as defined in claim 17, wherein:
- the system processor responds to the error condition signal by incrementing a count number with each instance where the first and second values differ by more than the predetermined amount;
- the system processor indicates the error condition upon the count number reaching a predetermined threshold.

25. A method as defined in claim 24, wherein:
- the system processor resets the count number to a predetermined count value upon the first and second values not differing by the predetermined amount within a predetermined number of most recent comparisons.

26. A method as defined in claim 24, wherein:
- the system processor increments the count number only with each instance where the first and second values differ by the predetermined amount within a predetermined number of most recent comparisons.

27. A method of evaluating functionality of an electrosurgical generator which delivers electrosurgical output power and which includes a control processor for controlling the delivery of the output power, a monitor processor for monitoring performance of the electrosurgical generator, and sensors for sensing current and voltage of the output power delivered, comprising:
- activating the electrosurgical generator to deliver the output power;
- sensing the current and the voltage at first periodic intervals to obtain a first set of measurements of the current and voltage of the output power delivered;
- sensing the current and the voltage at second periodic intervals to obtain a second set of measurements of the current and voltage of the output power delivered;
- recording the first and second sets of measurements;
- deactivating the electrosurgical generator to terminate the delivery of the output power;
- calculating a first value related to the output power delivered from the first set of recorded measurements by executing a first computation with the control processor;
- calculating a second value related to the output power delivered from the second set of recorded measurements by executing a second computation with the monitor processor;
- comparing the calculated first and second values to determine whether the calculated first and second values differ by a predetermined amount; and
- executing an error response upon determining that the calculated first and second values differ by the predetermined amount.

28. A method as defined in claim 27, wherein the electrosurgical generator also includes a system processor which oversees functionality of the control and monitor processors, further comprising:
- communicating the calculated first value from the control processor to the system processor;
- communicating the calculated second value from the monitor processor to the system processor;
- comparing the calculated first and second values by a computation executed by the system processor; and
- executing the error response by the system processor.

29. A method as defined in claim 27, further comprising:
- determining a time period between activating and deactivating the electrosurgical generator; and
- performing the comparing step only when the time period between activating and deactivating falls between a predetermined minimum time and a predetermined maximum time.

30. A method as defined in claim 27, further comprising:
- including within the error response executed at least one of logging an error occurrence, issuing an alert, and terminating the output power delivery.

31. A method as defined in claim 27, wherein the electrosurgical generator regulates the amount of output power delivered based on feedback information, and wherein:
- the sensors are connected to sense the current and the voltage of the output power delivered and are operative to supply current and voltage measurement signals related to the amount of output current and output voltage sensed, respectively;
- the control processor is receptive of the current and voltage measurement signals and performs the first computation based on the current and voltage measurement signals to derive the feedback information related to the output power delivered and to derive the first value;
- the monitor processor is receptive of the current and voltage measurement signals and performs the second computation based on the current and voltage measurement signals to derive the second value; and wherein the electrosurgical generator further comprises:

a communication path connecting the control and monitor processors over which the control and monitor processors communicate information including the first and second values, one of the control or monitor processors receiving the first and second values being a comparison processor; and wherein:

the comparison processor compares the first and second values and delivers an error condition signal when the first and second values differ by the predetermined amount; and the electrosurgical generator responds to the error condition signal by one of either indicating the error condition or terminating the delivery of output power as the error response.

32. A method as defined in claim 31, wherein the plurality of sensors includes:

a first current sensor for supplying a first current measurement signal used by the control processor in performing the first computation;

a second current sensor for supplying a second current measurement signal used by the monitor processor in performing the second computation;

a first voltage sensor for supplying a first voltage measurement signal used by the control processor in performing the first computation; and a second voltage sensor for supplying a second voltage measurement signal used by the monitor processor in performing the second computation.

33. A method as defined in claim 32, wherein the control and monitor processors are digital processors.

34. A method as defined in claim 33, wherein the electrosurgical generator further comprises:

a first analog to digital converter (ADC) connected to the first current sensor and to the first voltage sensor and operative to convert the first current measurement signal and the first voltage measurement signal into digital form;

a first direct memory access (DMA) controller;

a first buffer connected to the first ADC and to the first DMA controller, the first DMA controller placing the digital forms of the first current measurement signal and the first voltage measurement signal into the first buffer;

a second analog to digital converter (ADC) connected to the second current sensor and to the second voltage sensor and operative to convert the second current measurement signal and the second voltage measurement signal into digital form;

a second direct memory access (DMA) controller;

a second buffer connected to the second ADC and to the second DMA controller, the second DMA controller placing the digital forms of the second current measurement signal and the second voltage measurement signal into the second buffer; and wherein:

the control processor connected to the first buffer to read the digital forms of the first current measurement signal and the first voltage measurement signal from the first buffer to perform the first computation; and the monitor processor connected to the second buffer to read the digital forms of the second current measurement signal and the second voltage measurement signal from the second buffer to perform the second computation.

35. A method as defined in claim 31, wherein the electrosurgical generator further comprises:

a system processor which oversees functionality of the control and monitor processors, the system processor connected to the communication path to communicate with the control and monitor processors, the system processor rather than the monitor or control processor being the comparison processor which delivers the error condition signal.

36. A method as defined in claim 35, wherein the electrosurgical generator further comprises:

an alarm connected to the system processor and responsive to the error condition signal to deliver an alarm.

37. A method as defined in claim 35, wherein:

the system processor responds to the error condition signal by logging an error occurrence.

38. A method as defined in claim 31, wherein:

the comparison processor responds to the error condition signal by incrementing a count number with each instance where the first and second values differ by more than the predetermined amount; and the comparison processor indicates the error condition upon the count number reaching a predetermined threshold.

39. A method as defined in claim 38, wherein:

the comparison processor resets the count number to a predetermined count value upon the first and second values not differing by the predetermined amount within a predetermined number of most recent comparisons.

40. A method as defined in claim 38, wherein:

the comparison processor increments the count number only with each instance where the first and second values differ by the predetermined amount within a predetermined number of most recent comparisons.

* * * * *